US006537805B1

(12) United States Patent
Melchner et al.

(10) Patent No.: US 6,537,805 B1
(45) Date of Patent: Mar. 25, 2003

(54) SELF-DELETING VECTORS

(76) Inventors: Harald Von Melchner, Universitätsklinikum, Abteilung Haematologie, Theodor-Stern-Kai7 060596, Frankfurt (DE); Thomas Andreu, Universitätsklinikum, Abteilung Haematologie, Theodor-Stern-Kai 7 60596, Frankfurt (DE); Christoph Ebensperger, Universitätsklinikum, Abteilung Haematologie, Theodor-Stern-Kai 7 60596, Frankfurt (DE)

( * ) Notice: Subject to any disclaimer, the term of this patent is extended or adjusted under 35 U.S.C. 154(b) by 0 days.

(21) Appl. No.: 09/509,654

(22) PCT Filed: May 25, 1999

(86) PCT No.: PCT/EP99/03607
§ 371 (c)(1),
(2), (4) Date: Jun. 12, 2000

(87) PCT Pub. No.: WO00/06758
PCT Pub. Date: Feb. 10, 2000

(30) Foreign Application Priority Data

Jul. 30, 1998 (DE) .......................................... 198 34 430

(51) Int. Cl.[7] ........................ C12N 15/00; C07H 21/02; C07H 21/04
(52) U.S. Cl. .................. 435/320.1; 536/23.1; 536/23.4; 536/24.1
(58) Field of Search .......................... 514/44; 536/23.1, 536/23.4, 24.1; 435/320.1, 325; 800/21

(56) References Cited

U.S. PATENT DOCUMENTS 5,929,307 A  *  7/1999  Hodges et al. .............. 800/303

FOREIGN PATENT DOCUMENTS

WO          WO 97/07223        2/1997

OTHER PUBLICATIONS

Q. Shi et al., Human Gene Therapy, "Modulation of the specificity and activity of a cellular promoter in an adenoviral vector," Mar. 1997, 8:403–410.*
H.–L. Tsai et al., Journal of Biological Chemistry, "Human cytomegalovirus immediate–early protein IE2 tethers a transcriptional repression domain to p53," Feb. 1996, vol. 271, No. 7, pp. 3534–3540.*
I. M. Verma et al., Nature, "Gene therapy–promises, problems and prospects," Reviews, Sep. 1997, vol. 389, pp. 239–242.*
W. F. Anderson, Nature, "Human gene therapy," Reviews, Apr. 1998, vol. 392, pp. 25–30.*
Miller and Whelan. "Progress in Transcriptionally Targeted and Regulatable Vectors for Genetic Therapy" Human Gene Therapy 8:803–815, 1997.

Massuda et al. "Regulated expression of the diphtheria toxin A chain by a tumor–specific chimeric transcription factor results in selective toxicity for alveolar rhabdomysarcoma cells" Proc. Natl. Acad. Sci. 14701–14706, 1997.
Ozaki et al. "Use of von Willebrand Factor Promoter to Transduce Suicidal Gene to Human Endothelial Cells, HUVEC" Human Gene Therapy 7:1483–1490, 1996.
Rossi et al. "Excision of Ets by an inductible site–specific recombinase causes differentiation of Myb–Ets–transformed hematopoietic progenitors" Current Biology 6(7): 866–872, 1996.
Ring et al. "Suicide gene expression induced in tumour cells transduced with recombinant adenoviral, retroviral and plasmid vectors containing the ERBB2 promotor" Gene Therapy 3:1094–1103, 1996.
Chemical Abstract 124:46836 (Abstract related to the Article by Bergemann et al. "Excision of specific DNA–sequences from integrated retroviral vectors via site–specific recombination" Nucleic Acids Research 23(21):4551–6, 1995.
Kern et al. "Oncogenic Forms of p53 Inhibit p53–Regulated Gene Expression" Science 256:827–830, 1992.
A. Hoffmann et al., Nucleic Acids Research, "Novel tetracycline–dependent expression vector with low basa. expression and potent regulatory properties in various mammalian cell lines," 1997 Oxford Univ. Press, vol. 25, No. 5, pp. 1078–1079.*
M. Gossen et al., Proc.Natl.Acad.Sci. USA, "Tight control of gene expression in mammalian cells by tetracycline–responsive promoters," Cell Biology, Jun. 1992, vol. 89, pp. 5547–5551.*
U. Santhanam et al., Proc. Natl. Acad. Sci. USA, "Repression of the interleukin 6 gene promoter by p53 and the retinoblastoma susceptibility gene product," Biochemistry, Sep. 1991, vol. 88, pp. 7605–7609.*
J. Bergemann et al., Nucleic Acids Research, Excision of specific DNA –sequences from integrated retroviral vectors via site–specific recombination, 1995, vol. 23, No. 21, pp. 4451–4456.*

* cited by examiner

Primary Examiner—Deborah Crouch
Assistant Examiner—Joseph Woitach
(74) Attorney, Agent, or Firm—Needle & Rosenberg, P.C.

(57) ABSTRACT

The present invention relates to vectors for cancer therapy which as a result of genetic differences between normal and transformed cells selectively eliminate the latter. This is made possible by integrating a sequence-specific recombinase into a viral or non-viral expression vector whose expression is controlled by a transcription factor which has mutated in tumor cells and is therefore inactive, and also by a suicide gene which is flanked by at least one recombinase-specific target sequence. Through the transcription factor-mediated activation of the sequence-specific recombinase the vector is eliminated from untransformed cells together with the suicide gene. The vector is, however, not eliminated from tumor cells in which the transcription factor is inactive, and expresses the suicide gene. After contact with a corresponding prodrug these cells are selectively killed off.

72 Claims, 7 Drawing Sheets

SELF-DELETING VECTORS

The present application claims priority to German Application 198 34 430.9, filed Jul. 30, 1998.

The present invention relates to a recombinant vector, to a pharmaceutical composition containing the vector according to the invention, to the use of the vector according to the invention for treating tumor patients and to transduced eukaryotic cells.

So far benign and malign tumors have predominantly been treated either invasively, i.e. by surgical removal of the tumor, or conservatively, e.g. by administration of cytostatics or radiation of the organs affected, or by a combination of said methods. Great successes have already been achieved with these therapeutical possibilities because of permanently improving surgical techniques and a tremendous development in the field of cytostatics.

Nevertheless, the chances of success in the treatment of a tumor by said therapeutical methods vary considerably and are unpredictable. Moreover, each of the three methods has serious drawbacks. For instance, the surgical removal of a tumor and possibly the incision of healthy tissue greatly affects the patient because of the surgery itself. It is only in exceptional cases that the treatment with cytostatics and the radiation of tumors can be restricted to the target cells proper, so that it is almost unavoidable to subject healthy cells and healthy tissue to the treatment as well. A treatment with cytostatics means the inhibition of mitoses, which e.g. has the unpleasant side effect of alopecia. Both cytostatic treatment and radiation therapy may entail childlessness in patients of child-bearing and procreative age.

On account of the above-mentioned impairments attempts have already been made to transport therapeutics, in particular cytostatics, in a targeted manner to tumor cells and to have them internalized by said cells. An example thereof is the attempt to couple cytostatics to antibodies which bind to tumor cell-specific antigens. Despite the theoretical attractivity of such a proposal, this entails considerable difficulties, e.g. in obtaining sufficient amounts of antibodies, and also entails considerable risks, e.g. an immunological reaction to the foreign protein supplied.

A further approach is based on the knowledge about the role of transcription factors in the development of tumors. It is generally known that a few nuclear transcription factors serve to monitor the integrity of the cellular genome. When genomic DNA is damaged, said transcription factors will induce either a cell cycle arrest, which is required for repair, or apoptosis in the case of irreparable damage. Thus said transcription factors have an important tumor suppressor function. Many recent papers have been concerned with the transcription factor p53, in particular in connection with impaired p53 function in the development of cancer (Levine, 1997). The phenotype of p53$^{-/-}$ mice, produced by means of "gene targeting", demonstrates said connection: the absence of the protein results in an increased occurrence of spontaneous tumors (Donehower et al., 1992). Moreover, it could be demonstrated with the help of said mice that p53 plays a key role in the induction of apoptosis (Lowe et al., 1994).

In conventional tumor therapies, such as radiation or chemotherapy, it is this p53-mediated apoptosis induction that plays an important role (Lowe et al., 1993). On account of the accompanying resistance to cytostatics or radiation therapy, cancer types with mutated p53 (p53$^{mut}$) have a poor prognosis most of the time. In humans mutations of or deletions in p53 are observed in 50–80% of all cancer types (Levine et al, 1991). They always regard the DNA binding domain and entail loss in the p53 transactivator function.

The genetic difference between p53 molecules in normal and transformed cells has recently been exploited for the selective elimination of tumor cells. An adenovirus mutant which can only propagate in p53-deficient cells destroyed transplanted human p53$^{mut}$ tumors selectively and efficiently in nude mice experiments (Bischoff et al., 1996). In humans, however, an already existing immunity to adenoviruses could turn out to be a great problem. Since the majority of the population has already been immunized by preceding adenovirus infections, it could be that most of the patients intended for therapy will eliminate the therapeutical virus before it can develop its desired killing potential. Therefore, adenoviral vectors are only suited to a limited degree for use in gene therapy.

Starting from said prior art, it has been the object of the present invention to provide ways and means to fight tumor cells in a targeted manner.

According to the invention, this object is achieved by a recombinant vector comprising:
(a) at least one first transcription cassette containing a sequence coding for a recombinase, a minimal promoter MP functionally linked thereto, a transcription factor binding site and optionally a polyadenylation sequence, wherein the minimal promoter MP depends on the activation by one or several transcription factors,
(b) at least one second transcription cassette containing a suicide gene, a promoter P functionally linked thereto and optionally a polyadenylation sequence;
(c) a 5'-flanked sequence and/or a 3'-flanked sequence, wherein the 5'-and/or 3'-flanked sequence contains a recombinase target sequence.

The vector according to the invention permits the targeted and selective elimination of tumor cells in that a suicide gene is introduced by the vector into the cells, said gene being immediately eliminated in healthy cells by expression of recombinase whereas it can be activated in tumor cells with inactive transcription factors and leads to cell death (i) by expression of the suicide protein, (ii) by transcription of antisense RNA or (iii) by production of cytopathogenic virus.

In the context of the present invention the term "vector" means a linear or circular nucleic acid molecule which may consist of deoxyribonucleic acid and also of ribonucleic acid. Vectors suited for gene therapy, which may serve as starting material for the inventive vectors, are known in the prior art. Preferred vectors are vectors derived from viral or retroviral genomes because these can be packaged into viruses and can easily be introduced into cells by transduction. Vectors on a non-viral basis are also possible, but require further transfection measures. Suitable vectors would e.g. be fully synthetic vectors or vectors transduced by attenuated bacteria.

"Replication competence" means the ability of a vector to replicate in host cells. A very high replication competence with respect to mammalian cells is e.g. found in adenovirus, retroviruses, such as mouse leukemia virus MuLV, in particular Moloney mouse leukemia virus (MoMuLV). The invention generally comprises vectors with replication competence in eukaryotic cells. If the vectors are retroviruses, infectious retroviruses are preferred.

"Transcription cassettes" are nucleic acid units which apart from the sequence coding for a protein contain the necessary regulatory regions, e.g. promoter or minimal promoter with transcription factor binding site and polyadenylation sequences. The first transcription cassette may be located 5' or 3' relative to the second transcription cassette.

A "minimal promoter" is a natural or synthetic promoter or enhancer which can only activate the gene expression in the presence of a specific transcription factor. It contains at least one natural or synthetic transcription factor binding site.

A "transcription factor binding site" is a natural or synthetic nucleic acid sequence to which a transcription factor required for activating a minimal promoter can bind.

A "recombinase" is a natural or synthetic enzyme which recognizes and cuts specific target sequences and recombines the same with one another. Examples thereof are the Cre recombinase from the P1 coliphage (Sternberg and Hamilton, 1981) and the Flp recombinase from *S. cerevisiae* (Broach and Hicks, 1980).

"A target sequence" is a natural or synthetic sequence which can specifically be recognized by a recombinase. Examples thereof are the loxP sequences from the P1 coliphage (Gu et al., 1993; Sauer and Henderson 1988, Sternberg and Hamilton, 1991) and the FRT sequences from *S. cerevisiae* (Broach and Hicks, 1980, Golic and Lindquist, 1989; O'Gorman et al, 1991).

A "suicide gene" is a nucleic acid sequence which leads to cell death by transcription and possibly expression. In the vector according to the invention, it is present as part of a transcription cassette, i.e. in combination with a promoter and optionally a polyadenylation sequence.

Under one aspect of the present invention it is intended that the suicide gene is partly or completely complementary to an essential gene. The mRNA of the suicide gene produced by transcription is capable of hybridizing with the mRNA of the essential cellular gene. Consequences of the mRNA hybridization are translation arrest of the essential cellular gene and/or RNase-H activation with subsequent cell death. The essential cellular gene can be selected from cyclins and anti-apoptotic proteins, such as Bcl-2.

A further mechanism of action of the suicide gene as is intended according to the invention is that the suicide gene codes a cytopathogenic virus, such as Semliki forest virus, which kills the cell. Furthermore, the suicide gene may comprise a nucleic acid sequence coding for a suicide protein.

A "suicide protein" is a natural or artificial polypeptide product which directly or indirectly leads to cell death. The indirect effect is e.g. based on the interaction with a non-toxic agent precursor so that the precursor is converted into a toxic agent which is able to trigger the death of a cell. The suicide protein may be an antigen, such as influenza hemagglutinin or foreign MHC antigens. The direct effect is here based on the stimulation of an immune response directed against the tumor cell.

With the vectors according to the invention it is possible for the first time to eliminate tumor cells with a defective transcription factor in a targeted and direct manner. The basis for the selectivity of the vector according to the invention is that the recombinase coded by the first transcription factor can only be expressed in cells with an intact transcription factor. In tumor cells with a defective transcription factor there is no binding of the transcription factor to the transcription factor binding site associated with the minimal promoter. Since the minimal promoter requires activation by the transcription factor, there is no transcription and thus also no expression of the gene encoded by the first transcription cassette, i.e. the recombinase. In contrast thereto, the coding sequence of the second transcription cassette, i.e. the suicide gene, can be transcribed because the promoter which is functionally linked to said gene is independent of any activation by a transcription factor. After having come into contact with an agent precursor, the suicide protein now expressed will metabolize said precursor, thereby contributing to the production of a toxic agent. The metabolism product will subsequently cause the death of the respectively affected cell. Alternatively, a cell type-specific antisense RNA or a virus could lead to cell death.

By contrast, in healthy cells, i.e. in cells with an intact transcription factor, the factor can bind to the transcription factor binding site so that the protein coded by the first transcription cassette, i.e. the recombinase, is expressed. On account of the recombinase target sequences which are e.g. a priori provided by the vector and which flank the region of the transcription cassette, the region located between the target sequences with the first and second transcription cassettes is immediately deleted. In the case of retroviral vectors the LTR and thus the recombinase target sequence(s) are doubled by the integration. The region located between the target sequences is also deleted. What is left in the case of a healthy cell is just a copy of the target sequence, optionally together with the LTR per previous integration site of the vector.

The transcription factor as mentioned may be any transcription factor with a defect effecting a restriction or complete elimination of the transactivator capacity. A known example of a transcription factor whose DNA binding domain in tumor cells is relatively often changed in such a way that DNA binding and thus transactivation no longer take place is the said factor p53.

In human tumors the p53 mutations are always found in the DNA binding domain. This often leads to a loss in the DNA binding capacity and thus the transactivator function of the protein. p53-binding consensus sequences were found in a number of promoters and characterized. Moreover, p53 regulates, inter alia, the expression of p21 (WAF1) (el-Deiry et al. 1994), bax (Miyashita and Reed, 1995) and IGF-BP3 (Buckbinder et al. 1995). Such a p53-binding consensus sequence is e.g. the PG motif (CCTGCCTGGACTTGCCTG) (el-Deiry et al, 1992). The inventors and others have shown that said motif ($PG_n$) in connection with a minimal promoter (MP) makes the expression of a reporter gene p53-inducible. Such an induction is not possible with mutated p53. This has inter alia been demonstrated for the combinations $PG_n$-CMVMin-CAT (chloramphenicol acetyl transferase) (Kern et al., 1992) and pg13-SV40Min-SEAP (secreted alkaline phosphatase). The p53-binding consensus sequence pg13 is preferred for the purposes of the present invention.

In one embodiment of the invention the flanking sequences consist essentially of the recombinase target sequences. These may be natural or synthetic sequences which are recognized by a natural or recombinant recombinase.

In a preferred embodiment the vector of the invention is derived from a retrovirus. Retroviruses are RNA viruses whose replication involves a DNA intermediate. The viral RNA genome is flanked by short repeated sequences (repeats, R) and non-repeated sequences (unique sequences, U5 and U3) which control the DNA synthesis, the integration of the virus genome in the host genome, the transcription and the RNA processing. These control regions have provided thereinbetween coding sequences for the most important structural proteins of the virus particle, namely gag and env, and for further enzymes packaged in the particle (pol, protease, reverse transcriptase and integrase). Shortly after infection the viral RNA is translated by the reverse transcriptase into DNA. Prior to integration the terminal sequences of the viral genome are doubled so that the retroviral genome is flanked by long terminal repeated sequences (long terminal repeats, LTR) which contain each a U3 region, R and a U5 region. The linear molecules are then integrated into the genome.

After integration of the reversely transcribed virus genome into the host genome, one talks about a provirus. The provirus is replicated together with the cellular host DNA and transcribed like a cellular gene. The provirus transcription is controlled by promoter and enhancer sequences which are in the U3 region of the 5' LTR. Polyadenylated transcripts begin at the transition between U3 and R in the 5' LTR and end in the R of the 3' LTR which contains the polyadenylation signal.

Provided that specific control sequences remain within the LTRS, the retroviral genome can be exchanged for foreign DNA without impairing its ability to replicate in cells which express the proteins required for reverse transcription, integration and particle formation. To provide the enzymes required for the replication machinery, the vector DNA is transfected in cell lines which contain either complete retroviral genomes or helper viruses. The helper viruses cannot aggregate in particles due to a deletion between U5 and gag. As a consequence, only recombinant transcripts are packaged and released from the cells in virus particles. On account of said technical possibilities, retroviral vectors are preferred as vectors for gene therapy.

In the case of a vector derived from retroviruses, the 5'- and/or 3'-flanking sequences comprise complete or partial LTR regions. The at least one recombinase target sequence is here preferably in the U3 or U5 region of the 5' and/or 3' LTR. If the recombinase target sequence is outside the LTR, at least 2 recombinase target sequences are required. The transcription cassettes, however, are preferably outside the LTR. In the case of non-retroviral vectors at least two recombinase target sequences are provided.

The first transcription cassette contains, inter alia, a sequence coding for a recombinase. It is preferably arranged in the same transcription direction as the possibly underlying virus genome.

Any natural or synthetic protein with recombinase activity can be used as recombinase. In a preferred embodiment the recombinase encoded by the first transcription cassette is the recombinase Cre. The Cre recombinase was originally identified in coliphage P1 and is very well characterized. In preferred embodiments the recombinase target sequence for the recombinase Cre is the loxP sequence. Artificial recombinase target sequences which are recognized by the recombinase Cre can also be used. In an alternative embodiment Flp is used as recombinase. Flp derives originally from *S. cerevisiae*. It preferably recognizes FRT sequences from *S. cerevisiae*. These target sequences, in turn, can be replaced by artificial target sequences which are recognized by the recombinase Flp.

Every promoter depending on a transcription factor can be used as the minimal promoter. Preferred embodiments use ΔCMV (Gossen & Bujard, 1992) or ΔMMTV (Hoffmann et al., 1997). These promoters are truncated cytomegalovirus or mouse mammary tumor virus promoters which depend on a transactivation by transcription factors.

The suicide gene coded by the second transcription cassette is a thymidine kinase gene. According to the invention thymidine kinase from herpes simplex virus (HSV-TK) is particularly preferred. HSV-TK converts, for instance, added ganciclovir into a toxic metabolism product. However, all proteins that are known to produce a toxic agent from a non-toxic precursor agent after metabolization can be used as suicide proteins. A further example of such a suicide protein is cytosine deaminase.

In a further preferred embodiment the suicide gene is partly or completely complementary to an essential cellular gene. The mRNA produced by transcription of the suicide gene is capable of hybridizing with the mRNA of the essential cellular gene (antisense mechanism). Results of the mRNA hybridization are translation arrest and/or RNase-H activation which prevents the expression of the essential cellular gene and leads to cell death. Essential cellular genes, e.g., of the primary metabolism, are known to a person skilled in the art.

In a further preferred embodiment the suicide gene is able to produce a cytopathogenic virus by expression. Cytopathogenic viruses known to the person skilled in the art produce degenerative changes in the infected cells, for instance formation of giant cells, syncytia, inclusion bodies, vacuoles and granules, changes in the nucleus and lysis of the cells. An exemplary cytopathogenic virus is the Semliki forest virus.

The second transcription cassette is preferably arranged in the same transcription direction as the virus genome and the first transcription cassette; the first transcription cassette may here be located 5' or 3' relative to the second transcription cassette. In the case of an opposite arrangement, which is also possible, a further polyadenylation sequence must be provided for the second transcription cassette.

Any desired strong eukaryotic promoter may be used as promoter for the suicide gene. Preferred promoters are e.g. the LTR promoter of the Moloney mouse leukemia virus (MoMuLV). The person skilled in the art is aware of further promoters.

Moreover, in a further preferred embodiment the vectors according to the invention contain a selection marker cassette. Selection marker cassettes can e.g. be inserted into a U3 region. Said region can be used as evidence of the integration performed. A selection marker cassette illustrated in the examples is SV40Puro. Every other selection marker system that is transcribed and translated in eukaryotes and known to the person skilled in the art can however be used as well.

Additionally, the vectors according to the present invention can comprise any combination of transcription cassette, recombinase, promoter, transcription factor binding site, suicide gene, 5' flanking sequence, 3' flanking sequence, recombinase target sequence, and selection marker cassette described herein. Also, the present invention includes each embodiment of the vector described in PCT/EP99/03607 (WO 00/06758) which is hereby incorporated in its entirety by this reference.

Furthermore, the invention relates to pharmaceutical compositions which contain the vector according to the description herein and the claims. These pharmaceutical compositions are useful for the therapy of tumors which are characterized by the deficiency of a transcription factor. In preferred embodiments the vector in the therapeutic composition is packaged in a virus particle.

The vectors according to the invention are preferably replication-competent in pharmaceutical compositions. They are particularly preferably infectious, i.e. they are able to infect further cells.

The vector according to the invention can be used for treating tumor patients. In a preferred embodiment the intention is to kill tumor cells in a targeted manner by administration of the vector of the invention and subsequent administration of a precursor substance, such as ganciclovir, which is metabolizable by the suicide protein.

A further subject matter of the invention is a transduced eukaryotic cell which can be obtained by infecting a tumor cell comprising a deficient transcription factor, with a recombinant vector according to the description herein and the claims.

The following figures and examples will explain the invention:

Figure 1:
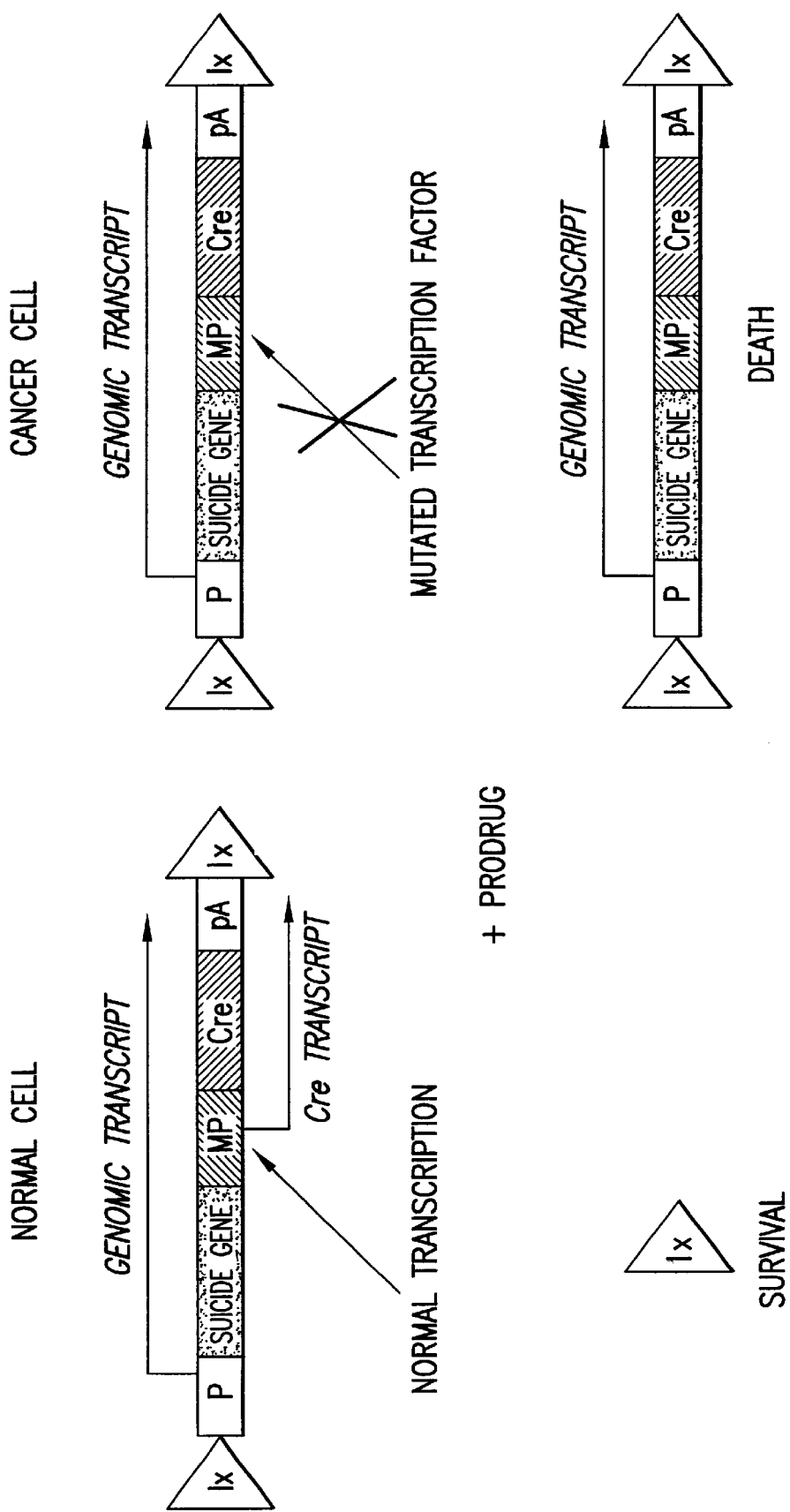
FIG. 1.
Figure 2:
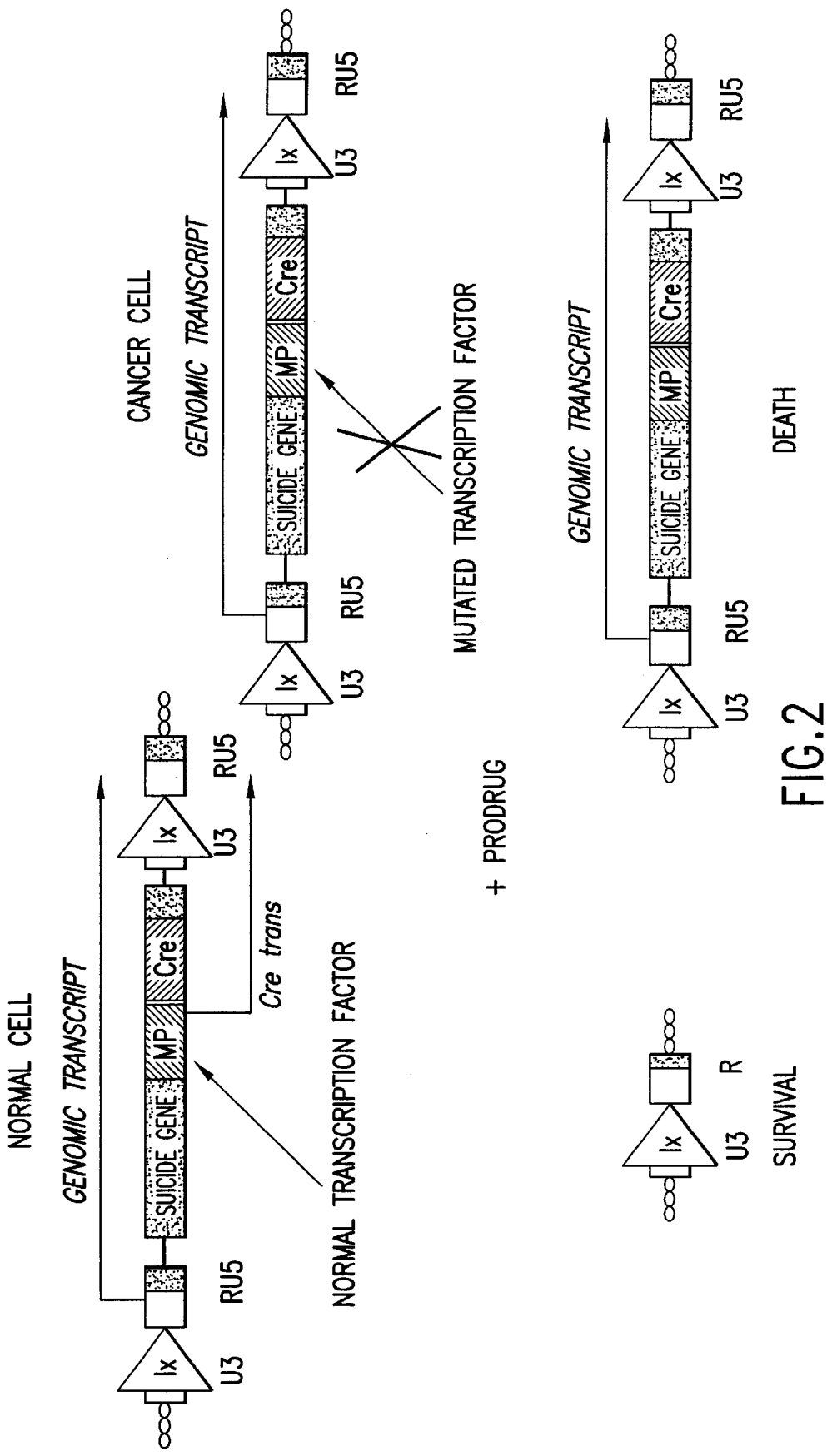

Vector concept and functional principle for selectively eliminating tumor cells. P=promoter, MP=minimal promoter, pA=polyadenylation sequence, Ix=lox P target sequence for the sequence-specific recombinase Cre.

FIG. 2:

Self-deleting retroviral vectors and functional principle for selectively eliminating tumor cells. After integration of the provirus, suicide gene and Cre recombinase are located between two loxP sites. In normal cells the expression of the Cre recombinase is activated and the majority of the integrated sequences is eliminated. By contrast, in cancer cells, the transcription factor is present in mutated form and cannot activate the transcription of the recombinase. As a consequence thereof, only infected cancer cells express the suicide gene. In this way only tumor cells become sensitive to the corresponding agent. U3RU5=retroviral control region with promoter, MP=minimal promoter, Ix=loxP target sequence for the sequence-specific recombinase Cre.

FIG. 3:

Self-deleting retroviral vectors for the selective elimination of tumor cells by ganciclovir. HSV-TK=herpes simplex virus 2 thymidine kinase gene, pg13=p53-binding consensus sequence, CMV=cytomegalovirus promoter, MMTV= mouse mammary tumor virus promoter, Ix=loxP target sequence for the sequence-specific recombinase Cre, SV40= simian virus 40 promoter, Puro=puromycin resistance gene.

FIG. 4:

Different behavior of the self-deleting retroviruses in normal and tumor cells. After doubling of the U3 region of the LTR after integration of the proviruses, the majority of the constructs are present between two loxP sites. p53-dependent transcription of the Cre enzyme results in the selective recombination in normal cells. In tumor cells p53 is present in mutated form and is thus not functionally present. A Cre-mediated recombination is thus not possible and the entire provirus is maintained. As a consequence, HSV-TK is expressed, making the tumor cells sensitive to ganciclovir. Normal cells do not react to ganciclovir because of the missing HSV-TK. HSV-TK=herpes simplex virus 2 thymidine kinase gene, pg13=p53-binding consensus sequence, CMV=cytomegalovirus promoter, MMTV= mouse mammary tumor virus promoter, Ix=loxP target sequence for the sequence-specific recombinase Cre, SV40= simian virus 40 promoter, Puro=puromycin resistance gene.

FIG. 5:

Cre reporter plasmid pSVpax1. Cre-mediated recombination results in the transcription of the lacZ gene of the SV40 promoter. SV=SV40 promoter, x=loxP target sequence for the sequence-specific recombinase Cre, Puro=puromycin resistance gene, lacZ=β-galactosidase gene, pA=polyadenylation sequence.

FIG. 6:

Transfection of the p53-dependent Cre expression plasmids into the reporter cell line Saos2/pSVpax1. A: transfection of ppg13ΔCMVCrepA alone (-p53) and with pSBC2-p53 (+p53). B: cotransfection of ppg13ΔMMTVCrepA alone (-p53) and with pSBC2-p53 (+p53).

FIG. 7:

PCR for the detection of Cre recombinase. Genomic DNA was amplified with Cre-specific primers. SV40-specific primers served as a control of the provirus integration.

EXAMPLES

Example 1

Production of a Saos2 Reporter Cell Line for Detecting Cre-mediated Recombination To obtain a cell line by which the activity of the Cre recombinase can be detected, human p53-deficient Saos2 osteosarcoma cells were stably transfected with the reporter construct pSVpaX1 by means of the Ca-phosphate coprecipitation method (Pear et al., 1993).

Figure 5:
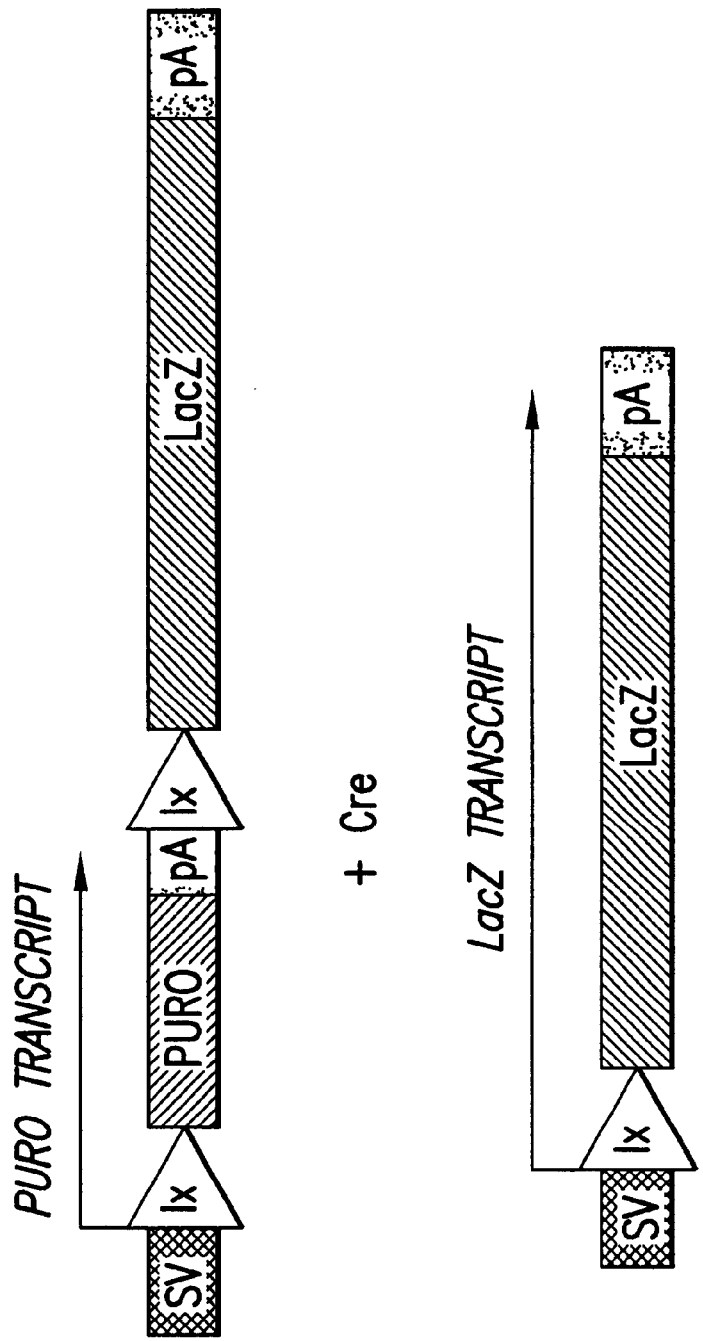

The reporter construct pSVpaX1 (Buchholz et al., 1996) consists of the lacZ gene which codes for an easily detectable protein (β-galactosidase). The lacZ gene is only transcribed by an SV40 promoter after Cre-mediated recombinase (FIG. 5).

A puromycin phosphotransferase resistance gene which is flanked by two loxP sites is positioned between the coding sequences of the SV40 promoter and the lacZ gene. The SV40 promoter transcribes the resistance gene in the non-recombined state, thereby permitting selection for the reporter construct. In the absence of Cre recombinase the puromycin-phosphotransferase sequences are removed between the loxP sites, and the lacZ gene is brought under the control of the SV40 promoter. Thus, the Cre recombinase activity can easily be detected by detection of the β-galactosidase expression in the cells (X-Gal staining).

The pSVpaX1-transfected cells were selected with 0.5 mg/ml puromycin (Sigma) for 7 days. The resulting transformants showed no background staining after incubation with X-Gal. Transfection with the Cre expression plasmid pMC-Cre yielded a clear lacZ-positive phenotype of the transfected cells.

Example 2

Production of p53-dependent Cre Expression Plasmids

We showed the p53 dependence for two different minimal promoters with the help of Cre expression plasmids. These minimal promoters consist of the p53-binding pg13 motif (Kern et al., 1992), coupled on the one hand to a shortened cytomegalovirus (ΔCMV) promoter (Gossen and Bujard, 1992) and, on the other hand, to a shortened murine mammary tumor virus (ΔMMTV) promoter (Hoffmann et al, 1997). The two expression plasmids were cloned in the following way:

1. Digestion of pBluescript (pBS) with the restriction enzyme ClaI and the Klenow enzyme and of pU3Cre (Russ et al., 1996) with NheI and Klenow enzyme. Ligation of the Cre fragment with the linearized vector yielded pBSCre.
2. Digestion of pBSCre and of pGLpg13Seap (C. Rinderele, Asta Medica AG) with SacI and EcoRI. The pg13 fragment was cloned as SacI/EcoRI fragment from pGlpg13Seap 5' from Cre into pBSCre. This yielded ppg13Cre.
3. Digestion of ppg13Cre with HindIII and Klenow enzyme. Ligations: 1. with the synthetic ΔCMV promoter piece (GGC CGG CCT ATA AGC AGA GCT CGT TTA GTG GCC) yielded ppg13ΔCMVCre; 2. with a PCR fragment of the ΔMMTV promoter (primer 5': CCT ATG TTA TTT TGG AAC TTA TCC, primer 3': AGG GCC CTG TTC GGG CGC C) yielded ppg13ΔMMTVCre.

4. Digestion of the two constructs (ppg13ΔCMVCre and ppg13ΔMMTVCre) with SalI and Klenow enzyme and of ppg13Seap with BamHI, SalI and Klenow enzyme. Ligation of the excised polyadenylation signal (pA) resulted in the two following p53-dependent Cre expression plasmids:

_ppg13ΔCMVCrepA

_ppg13ΔMMTVCrepA.

For the detection of the p53-dependent Cre-mediated recombination the Cre expression plasmids were transiently transfected with and without the p53 expression plasmid pSBC2-p53 into the p53$^{-/-}$-reporter cell line Saos2/pSVpax1. Transfection was carried out in accordance with a standard protocol by means of Ca-phosphate coprecipitation (Pear et al., 1993).

Figure 6A:
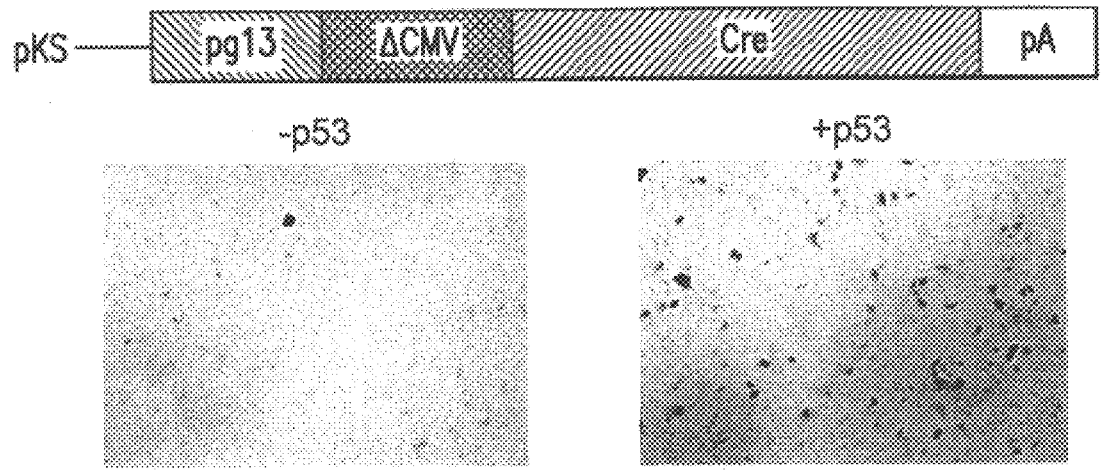
Figure 6B:
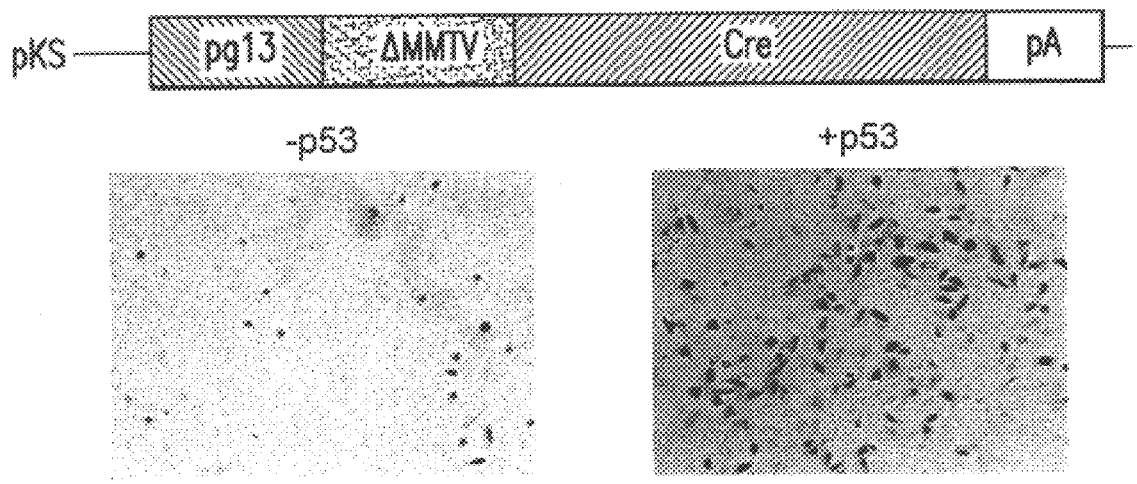

After 48 hours the cells were stained with X-Gal for detection of β-galactosidase. In both cases FIG. 6 clearly demonstrates that p53 significantly stimulated the Cre-mediated recombination of the reporter plasmid pSVpax1 and, as a consequence, the expression of β-galactosidase.

The results demonstrate that the two produced minimal promoters pg13ΔCMV and pg13ΔMMTV permit a p53-dependent expression of the Cre recombinase.

Example 3

Cloning of p53-regulated Self-deleting Retroviral Vectors

The cloning method leading to the p53-dependent self-deleting constructs shall briefly be described in the following:

1. Digestion of pBS and pGLpg13Seap with HindIII. Ligation of the vector with the pg13SV40 fragment yielded ppg13SV40.
2. Digestion of pU3TK (Russ et al. 1996b) with NheI and Klenow enzyme and of ppg13SV40 with SalI and Klenow enzyme. Ligation of the thymidine kinase (TK) cassette with the vector yielded pHSVTKpgSV40.
3. Digestion of pU3Cre with NheI and Klenow enzyme and of pTKpg13SV40 with XbaI and Klenow enzyme. Ligation of Cre with the vector yielded pHSVTKpgSV40Cre.
4. Digestion of pTKpg13SV40Cre with NotI, Klenow enzyme, then with XhoI, and of pBABEpuro (Russ et al. 1996b) with ClaI, Klenow enzyme and then with SalI. Ligation of the TKpg13SV40Cre cassette with the pBABE fragment yielded pHSVTKpgSV40CreU3RU5.
5. The IxSV40puro cassette was excised from the construct pggSV40CreIXSV40Puro (Russ et al., 1996a) with BamHI and ClaI and ligated into the corresponding restriction sites of pBS. This yielded pBSIxSV40Puro.
6. Digestion of pHSVTKpgSV40CreU3RU5 with NheI and pBSIxSV40Puro with SpeI and XbaI. Ligation of the IxSV40Puro cassette with the retroviral vector yielded pHSVTKpgSV40CreU3IxSV40Puro.

Figure 3:
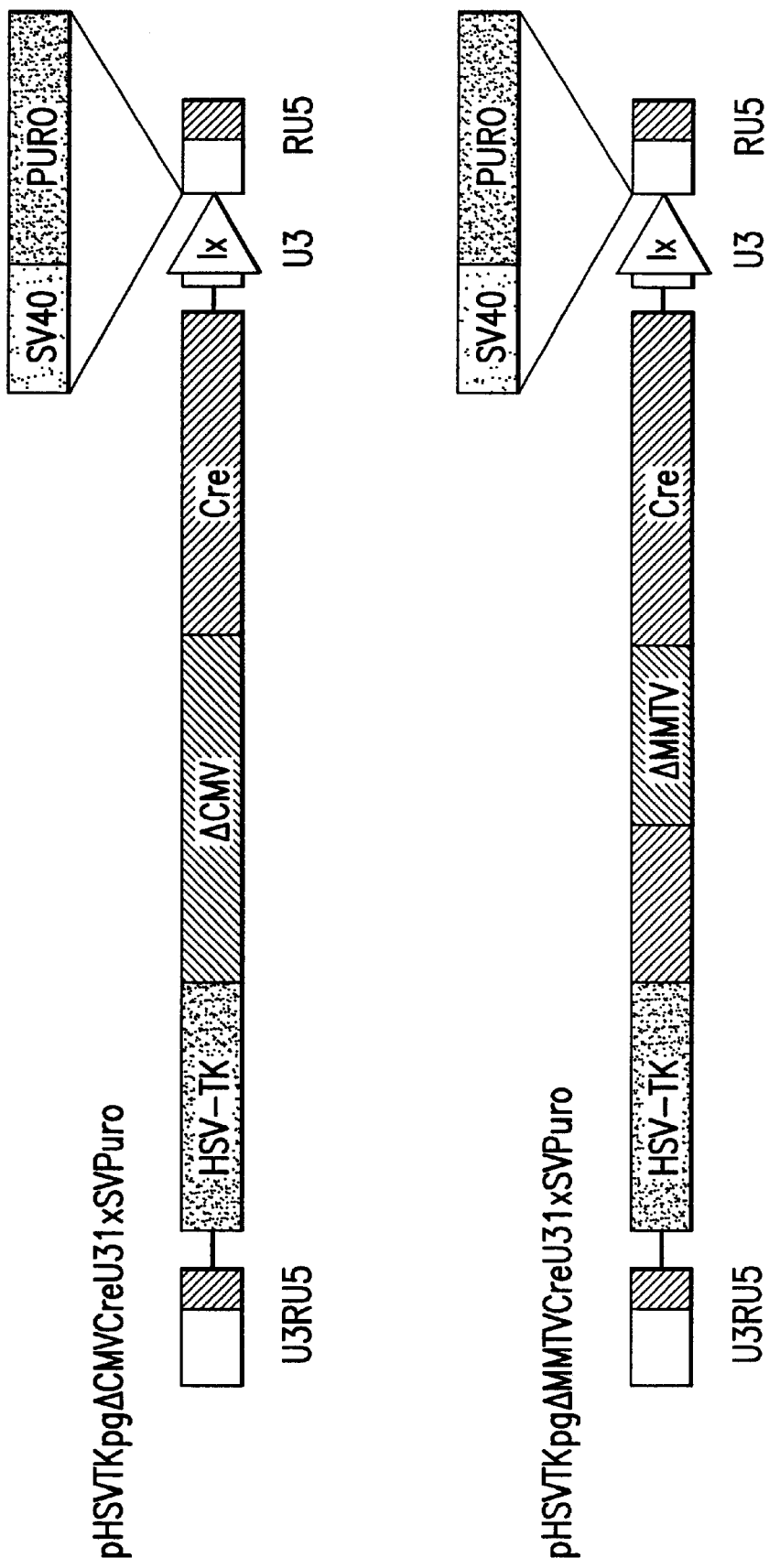

The minimal promoter pg13SV40 was exchanged for the minimal promoters pg13ΔCMV and pg13ΔMMTV in the following way:

Digestion of the plasmid pHSVTKpgSV40CreU3IxSV40Puro with BstBI and partial digestion with EcoRI. Digestion of the expression plasmids ppg13ΔCMVCrepA and ppg13ΔMMTVCrepA with the same restriction enzymes. Ligation of the corresponding fragments yielded the following p53-regulated self-deleting constructs (FIG. 3):

_pHSVTKpgΔCMVCreU3IxSV40Puro

_pHSVTKpgΔMMTVCreU3IxSV40Puro.

Figure 7:
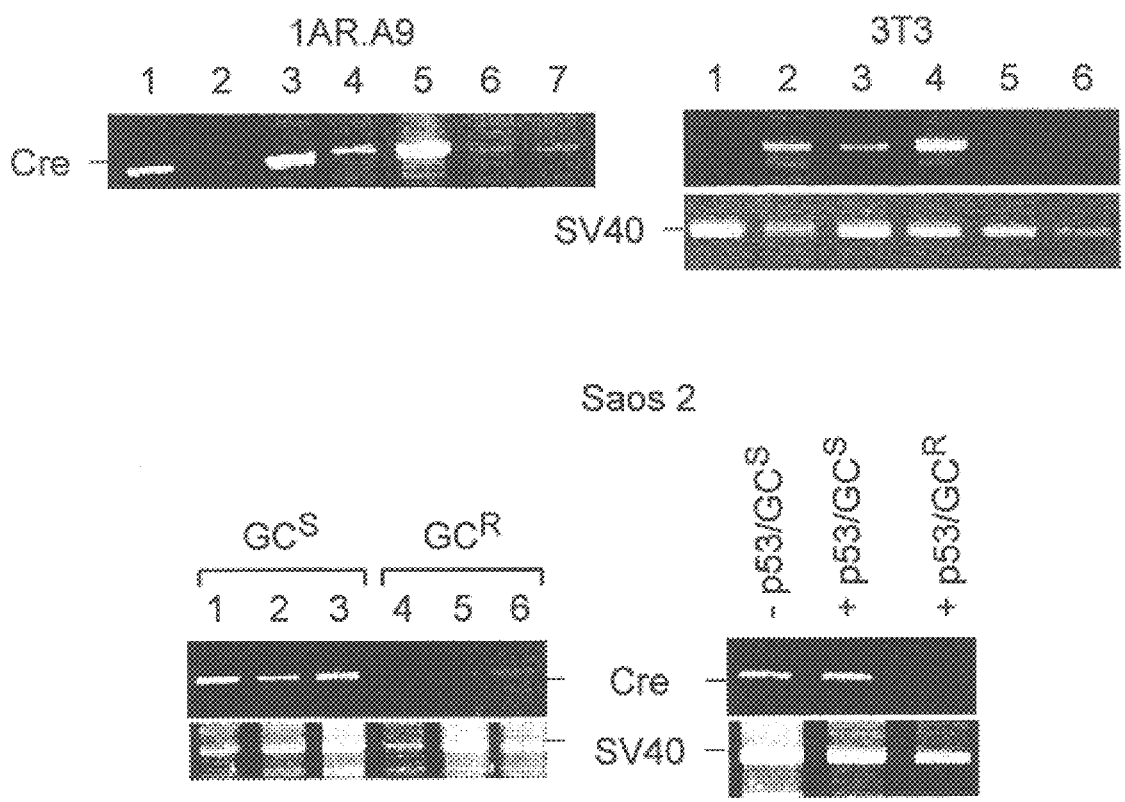

For detection that the Cre/loxP-mediated recombination also remains p53-dependent in the retroviral vectors pHSVTKpgΔCMVCreU3IxSV40Puro and pHSVTKpgΔMMTVCreU3IxSV40Puro, the plasmids were transiently transfected into Phoenix cells and packaged into retroviral particles (Pear et al. in press and on internet web page). With the virus-containing cell culture supernatants produced thereby, we infected Saos2 cells which contained no p53. After selection in puromycin (5 μg/ml) we could isolate provirus-containing single clones. For the detection of a possibly minute Cre expression in the absence of p53, individual clones were kept in 20 μM ganciclovir (GC, Syntex). Table 1 shows that 56% and 83%, respectively, of the provirus-expressed clones died in GC in dependence upon the respective minimal promoter. In all GC-sensitive clones, Cre DNA could be detected by means of specific PCR (FIG. 7). This means that no recombination took place in the majority of the infected Saos2 clones. In further tests GC-sensitive clones were transiently transfected with the wild-type p53 expression plasmid (pSBC2-p53). GC-surviving cells were again assayed by means of PCR for recombination. As illustrated in FIG. 7 by way of example, the GC-resistant cells no longer contained any Cre recombinase. These results furnish clear proof that the wild-type p53 is able to eliminate the sequences positioned between the proviral LTRs from the genome by activating the transcription of the Cre recombinase.

Example 4

Selective Killing of p53$^{-/-}$ Cells by Self-deleting Retroviral Vectors

Figure 4:
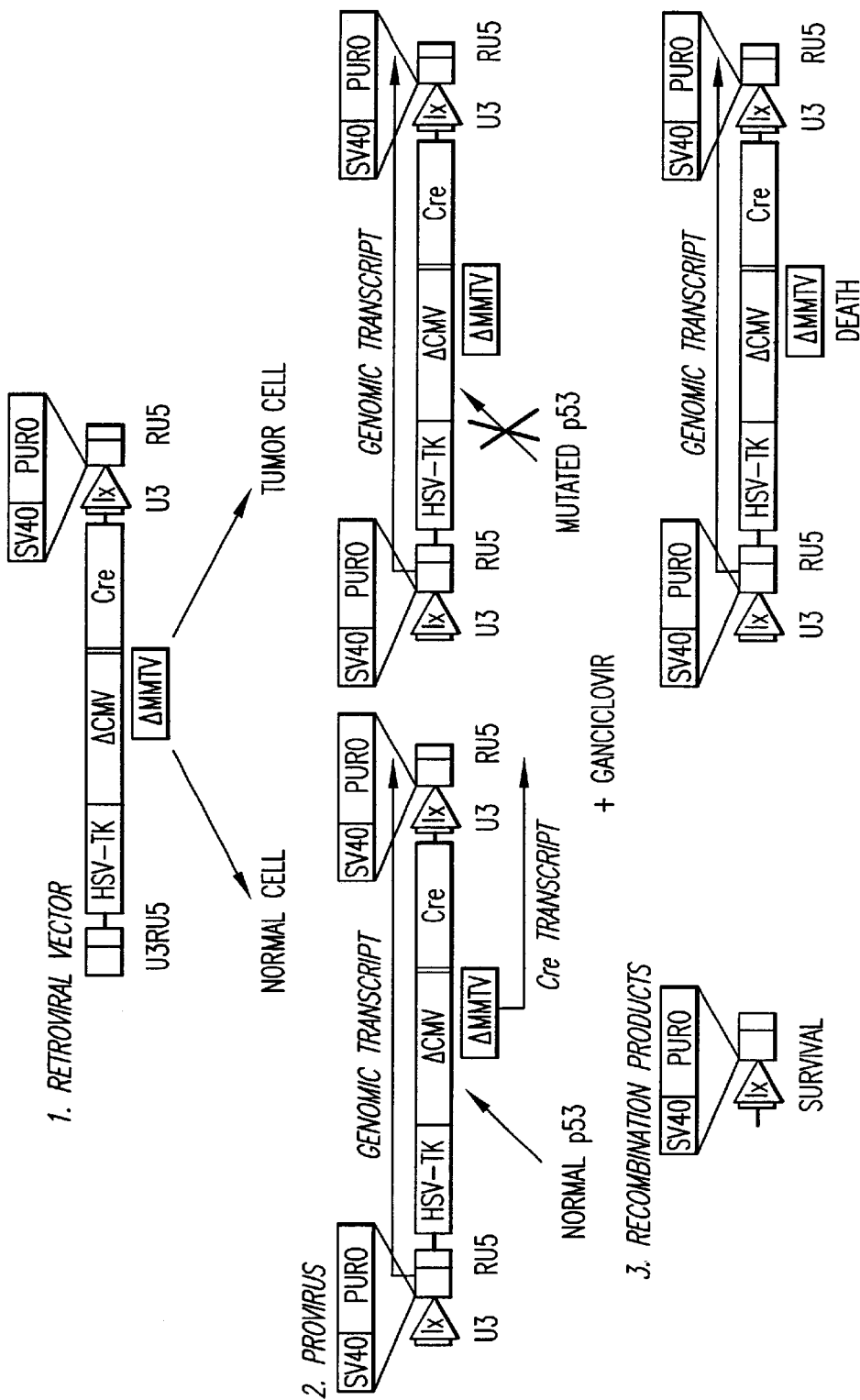

To answer the question whether endogenous p53 is also able to activate the Cre expression of the vectors, transformed mouse fibroblasts were, as described in Example 3, infected with the same retroviruses, and provirus-containing clones were isolated. The fibroblasts are on the one hand p53$^{-/-}$-1AR.A9 cells which derived from p53 knock-out mice (Lowe et al., 1994) and on the other hand conventional NIH3T3 cells expressing small amounts of wild-type p53. While 100% of all puromycin-resistant 1AR.A9 clones died because of the missing recombination in GC, 57% of the NIH3T3 cell clones survived (FIG. 7, Table 1). DNA tests showed that this phenotype was based on a Cre-mediated recombination which eliminated the majority of the provirus including HSV-TK (FIG. 4).

TABLE 1 p53-dependent ganciclovir resistance in virus-infected cells*

| cells | 1AR.A9 | | NIH3T3 | | Saos2 | |
|---|---|---|---|---|---|---|
| minimal.promoter | ΔCMV | ΔMMTV | ΔCMV | ΔMMTV | ΔCMV | ΔMMTV |
| surviving clones | 0/5 (0%) | 0/10 (0%) | nt | 4/7 (57%) | 9/16 (56%) | 15/18 (83%) |

*Puromycin-resistant clones were cultured in the presence of ganciclovir (20 mM) and the number of the surviving clones was determined after incubation for seven days.
nt: not tested

BIBLIOGRAPHY

Bischoff, J. R., D. H. Kim, A. Williams, C. Heise, S. Horn, M. Muna, L. Ng, J. A. Nye, A. Sampson-Johannes, A. Fattaey, and F. McCormick. 1996. An adenovirus mutant that replicates selectively in p53-deficient human tumor cells [see comments]. *Science* 274, 373–6.

Broach, J. R., and J. B. Hicks. 1980. Replication and recombination functions associated with the yeast plasmid, 2μ circle. *Cell* 21, 501–508.

Buchholz, F., L. Ringrose, P. O. Angrand, F. Rossi, and A. F. Stewart. 1996. Different thermostabilities of FLP and Cre recombinases: implications for applied site-specific recombination. *Nucleic Acids Res* 24, 4256–62.

Buckbinder, L., R. Talbott, S. Velasco-Miguel, I. Takenaka, B. Faha, B. R. Seizinger, and N. Kley. 1995. Induction of the growth inhibitor IGF-binding protein 3 by p53. *Nature* 377, 646–9.

Donehower, L. A., M. Harvey, B. L. Slagle, M. J. McArthur, C. A. Montgomery, Jr., J. S. Butel, and A. Bradley. 1992. Mice deficient for p53 are developmentally normal but susceptible to spontaneous tumours. *Nature* 356, 215–21.

el-Deiry, W. S., S. E. Kern, J. A. Pietenpol, K. W. Kinzler, and B. Vogelstein. 1992. Definition of a consensus binding site for p53. *Nat Genet* 1, 45–9.

el-Deiry, W. S., J. W. Harper, P. M. O'Connor, V. E. Velculescu, C. E. Canman, J. Jackman, J. A. Pietenpol, M. Burell, D. E. Hill, Y. Wang, and et al. 1994. WAF1/CIP1 is induced in p53-mediated G1 arrest and apoptosis. *Cancer Res* 54, 1169–74.

Golic, K. G., and S. Lindquist. 1989. The FLP recombinase of yeast catalyzes site-specific recombination in the Drosophila genome. *Cell* 59, 499–509.

Gossen, M., and H. Bujard. 1992. Tight control of gene expression in mammalian cells by tetracycline-responsive promoters. *Proc Natl Acad Sci USA* 89, 5547–5551.

Gu, H., Y. Zou, and K. Rajewsky. 1993. Independent control of immunoglobulin switch recombination at individual switch regions evidenced through Cre-loxP-mediated gene targeting. *Cell* 73, 1155–1164.

Hoffmann, A., M. Villalba, L. Journot, and D. Spengler. 1997. A novel tetracycline-dependent expression vector with low basal expression and potent regulatory properties in various mammalian cell lines. *Nucleic Acids Res* 25, 1078–1079.

Kern, S., J. Pietenpol, S. Thiagalingam, A. Seymour, K. Kinzier, and B. Vogelstein. 1992. Oncogenic forms of p53 inhibit p53-regulated gene expression. *Science* 256, 827–830.

Levine, A. J. 1997. p53, the cellular gatekeeper for growth and division. *Cell* 88, 323–31.

Levine, A. J., J. Momand, and C. A. Finlay. 1991. The p53 tumour suppressor gene. *Nature* 351, 453–6.

Lowe, S., S. Bodis, A. McClatchey, L. Remington, H. Ruley, D. Fisher, D. Housman, and T. Jacks. 1994. p53 status and the efficacy of cancer therapy in vivo. *Science* 266, 807–810.

Lowe, S. W., H. E. Ruley, T. Jacks, and D. E. Housman. 1993. p53-dependent apoptosis modulates the cytotoxicity of anticancer agents. *Cell* 74, 957–67.

Miyashita, T., and J. C. Reed. 1995. Tumor suppressor p53 is a direct transcriptional activator of the human bax gene. *Cell* 80, 293–9.

O'Gorman, S., D. T. Fox, and G. M. Wahl. 1991. Recombinase-mediated gene activation and site-specific integration in mammalian cells. *Science* 251, 13511355.

Pear, W., G. Nolan, M. Scott, and D. Baltimore. 1993. Production of high-titer helper-free retroviruses by transient transfection. *Proc Natl Acad Sci USA* 90, 8392–8396.

Pear, W., M. Scott, and G. Nolan. Rapid production of high titer, helper-free retroviruses using transient transfection. *Methods in Gene Therapy* in press und Internet Web page: httD://www.stanford.edu/group/nolan/NL-phoenix.html.

Russ, A., C. Friedel, K. Ballas, K. U, D. Zahn, K. Strebhardt, and H. v. Melchner. 1996a. Identification of genes induced by factor deprivation in hematopoietic cells undergoing apoptosis using gene-trap mutagenesis and site-specific recombination. *Proc Natl Acad Sci USA* 93, 15279–15284.

Russ, A., C. Friedel, M. Grez, and H. v. Melchner. 1996b. Self-deleting retrovirus vectors for gene therapy. *J Virol* 70, 4927–4932.

Sauer, B., and N. Henderson. 1988. Site-specific recombination in mammalian cells by the Cre recombinase of bacteriophage P1. *Proc. Natl. Acad. Sci. USA* 85, 5166–5170.

Sternberg, N., and D. Hamilton. 1981. Bacteriophage P1 site-specific recombination. I. Recombination between loxP sites. *J. Mol. Biol.* 150, 467–486.

What is claimed is:

1. A recombinant vector comprising:
   (a) at least one first transcription cassette containing a sequence coding for a recombinase, a minimal promoter MP functionally linked thereto, a transcription factor binding site and optionally a polyadenylation sequence, wherein the minimal promoter MP depends on the activation by one or several transcription factors, wherein the transcription factor binding site binds the transcription factor p53;
   (b) at least one second transcription cassette containing a suicide gene, a promoter P functionally linked thereto and optionally a polyadenylation sequence;
   (c) a 5' flanking sequence and/or a 3' flanking sequence, wherein the 5' and/or 3' flanking sequence contains a recombinase target sequence.

2. The recombinant vector according to claim 1, wherein the 5' or 3' flanking sequence consists essentially of recombinase target sequences.

3. The recombinant vector according to claim 1, wherein the vector is a retroviral vector.

4. The recombinant vector according to claim 3, wherein the minimal promoter MP is ΔCMV or ΔMMTV.

5. The recombinant vector according to claim 4, wherein the suicide gene is a thymidine kinase gene.

6. The recombinant vector according to claim 5, wherein the vector contains at least one selection marker cassette.

7. The recombinant vector according to claim 4, wherein the vector contains at least one selection marker cassette.

8. The recombinant vector according to claim 3, wherein the suicide gene is a thymidine kinase gene.

9. The recombinant vector according to claim 8, wherein the vector contains at least one selection marker cassette.

10. The recombinant vector according to claim 3, wherein the vector contains at least one selection marker cassette.

11. The recombinant vector according to claim 3, wherein the 5' and/or 3' flanking sequences contain complete or partial retroviral LTR regions, and at least one recombinase target sequence is embedded in the U3 and/or U5 region of the 5' and/or 3' LTR, wherein at least one of the U3 or U5 region is present in the LTR region.

12. The recombinant vector according to claim 11, wherein the recombinase is Cre.

13. The recombinant vector according to claim 12, wherein the recombinase target sequence is loxP.

14. The recombinant vector according to claim 13, wherein the suicide gene is a thymidine kinase gene.

15. The recombinant vector according to claim 14, wherein the vector contains at least one selection marker cassette.

16. The recombinant vector according to claim 13, wherein the minimal promoter MP is ΔCMV or ΔMMTV.

17. The recombinant vector according to claim 16, wherein the vector contains at least one selection marker cassette.

18. The recombinant vector according to claim 13, wherein the vector contains at least one selection marker cassette.

19. The recombinant vector according to claim 12, wherein the minimal promoter MP is ΔCMV or ΔMMTV.

20. The recombinant vector according to claim 19, wherein the vector contains at least one selection marker cassette.

21. The recombinant vector according to claim 12, wherein the suicide gene is a thymidine kinase gene.

22. The recombinant vector according to claim 21, wherein the vector contains at least one selection marker cassette.

23. The recombinant vector according to claim 12, wherein the vector contains at least one selection marker cassette.

24. The recombinant vector according to claim 11, wherein the recombinase is Flp.

25. The recombinant vector according to claim 24 wherein the recombinase target sequence is FRT.

26. The recombinant vector according to claim 25, wherein the suicide gene is a thymidine kinase gene.

27. The recombinant vector according to claim 26, wherein the vector contains at least one selection marker cassette.

28. The recombinant vector according to claim 25, wherein the minimal promoter MP is ΔCMV or ΔMMTV.

29. The recombinant vector according to claim 28, wherein the vector contains at least one selection marker cassette.

30. The recombinant vector according to claim 25, wherein the vector contains at least one selection marker cassette.

31. The recombinant vector according to claim 24, wherein the minimal promoter MP is ΔCMV or ΔMMTV.

32. The recombinant vector according to claim 31, wherein the vector contains at least one selection marker cassette.

33. The recombinant vector according to claim 24, wherein the suicide gene is a thymidine kinase gene.

34. The recombinant vector according to claim 33, wherein the vector contains at least one selection marker cassette.

35. The recombinant vector according to claim 24, wherein the vector contains at least one selection marker cassette.

36. The recombinant vector according to claim 12, further comprising the recombinase Flp.

37. The recombinant vector according to claim 36, wherein the minimal promoter MP is ΔCMV or ΔMMTV.

38. The recombinant vector according to claim 37, wherein the vector contains at least one selection marker cassette.

39. The recombinant vector according to claim 36, wherein the suicide gene is a thymidine kinase gene.

40. The recombinant vector according to claim 39, wherein the vector contains at least one selection marker cassette.

41. The recombinant vector according to claim 36, wherein the vector contains at least one selection marker cassette.

42. The recombinant vector according to claim 11, wherein the minimal promoter MP is ΔCMV or ΔMMTV.

43. The recombinant vector according to claim 42, wherein the suicide gene is a thymidine kinase gene.

44. The recombinant vector according to claim 43, wherein the vector contains at least one selection marker cassette.

45. The recombinant vector according to claim 42, wherein the vector contains at least one selection marker cassette.

46. The recombinant vector according to claim 11, wherein the suicide gene is a thymidine kinase gene.

47. The recombinant vector according to claim 46, wherein the vector contains at least one selection marker cassette.

48. The recombinant vector according to claim 11, wherein the vector contains at least one selection marker cassette.

49. The recombinant vector according to claim 3, wherein the recombinase is Cre.

50. The recombinant vector according to claim 49, wherein the recombinase target sequence is loxP.

51. The recombinant vector according to claim 50, wherein the minimal promoter MP is ΔCMV or ΔMMTV.

52. The recombinant vector according to claim 51, wherein the vector contains at least one selection marker cassette.

53. The recombinant vector according to claim 50, wherein the suicide gene is a thymidine kinase gene.

54. The recombinant vector according to claim 53, wherein the vector contains at least one selection marker cassette.

55. The recombinant vector according to claim 50, wherein the vector contains at least one selection marker cassette.

56. The recombinant vector according to claim 49, wherein the suicide gene is a thymidine kinase gene.

57. The recombinant vector according to claim 56, wherein the vector contains at least one selection marker cassette.

58. The recombinant vector according to claim 49, wherein the minimal promoter MP is ΔCMV or ΔMMTV.

59. The recombinant vector according to claim 58, wherein the vector contains at least one selection marker cassette.

60. The recombinant vector according to claim 49, wherein the vector contains at least one selection marker cassette.

61. The recombinant vector according to claim 3, wherein the recombinase is Flp.

62. The recombinant vector according to claim 61 wherein the recombinase target sequence is FRT.

63. The recombinant vector according to claim 62, wherein the minimal promoter MP is ΔCMV or ΔMMTV.

64. The recombinant vector according to claim 63, wherein the vector contains at least one selection marker cassette.

65. The recombinant vector according to claim 62, wherein the suicide gene is a thymidine kinase gene.

66. The recombinant vector according to claim 65, wherein the vector contains at least one selection marker cassette.

67. The recombinant vector according to claim 62, wherein the vector contains at least one selection marker cassette.

68. The recombinant vector according to claim 61, wherein the minimal promoter MP is ΔCMV or ΔMMTV.

69. The recombinant vector according to claim 68, wherein the vector contains at least one selection marker cassette.

70. The recombinant vector according to claim 61, wherein the suicide gene is a thymidine kinase gene.

71. The recombinant vector according to claim 70, wherein the vector contains at least one selection marker cassette.

72. The recombinant vector according to claim 61, wherein the vector contains at least one selection marker cassette.

* * * * *

SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Description of artificial sequence:
    /note=synthetic construct

<400> SEQUENCE: 1
cctgcctgga cttgcctg                                                  18

<210> SEQ ID NO 2
<211> LENGTH: 33
<212> TYPE: DNA
<213> ORGANISM: Artificial Sequence
<220> FEATURE:
<223> OTHER INFORMATION: Description of artificial sequence:
    /note=synthetic construct

<400> SEQUENCE: 2
ggccggccta taagcagagc tcgtttagtg gcc                                 33

<210> SEQ ID NO 3
<211> LENGTH: 24
<212> TYPE: DNA
<213> ORGANISM: Artificial Sequence
<220> FEATURE:
<223> OTHER INFORMATION: Description of artificial sequence:
    /note=synthetic construct

<400> SEQUENCE: 3
cctatgttat tttggaactt atcc                                           24

<210> SEQ ID NO 4
<211> LENGTH: 19
<212> TYPE: DNA
<213> ORGANISM: Artificial Sequence
<220> FEATURE:
<223> OTHER INFORMATION: Description of artificial sequence:
    /note=synthetic construct

<400> SEQUENCE: 4
agggccctgt tcgggcgcc                                                 19